United States Patent [19]

Fujiwhara et al.

[11] Patent Number: 5,041,667

[45] Date of Patent: Aug. 20, 1991

[54] PROCESS FOR PRODUCING CHLOROPHENYLHYDRAZINE COMPOUNDS

[75] Inventors: Mitsuto Fujiwhara; Tamotsu Kojima, both of Tokyo, Japan

[73] Assignee: Konishiroku Photo Industry Co., Ltd., Tokyo, Japan

[21] Appl. No.: 878,690

[22] Filed: Jun. 26, 1986

[30] Foreign Application Priority Data

Jun. 27, 1985 [JP]  Japan ................. 60-141327
Jun. 27, 1985 [JP]  Japan ................. 60-141328
Jun. 27, 1985 [JP]  Japan ................. 60-141329
Jun. 27, 1985 [JP]  Japan ................. 60-141330
Sep. 20, 1985 [JP]  Japan ................. 60-207846
Sep. 20, 1985 [JP]  Japan ................. 60-207847

[51] Int. Cl.$^5$ .......................... C07C 241/02
[52] U.S. Cl. ...................... 564/314; 544/5; 544/312; 544/385; 546/219; 548/123; 548/183; 548/210; 548/227; 548/311; 562/439
[58] Field of Search ............... 584/314; 544/5, 312, 544/385; 546/219; 548/123, 183, 210, 227, 311

[56] References Cited

U.S. PATENT DOCUMENTS 1,960,275  5/1934  Miller ........................... 260/124
2,973,386  2/1961  Weldon ......................... 564/412 X
4,420,486 12/1983  Ohyama et al. ................ 564/413 X
4,447,647  5/1984  Werner et al. ................. 564/412

FOREIGN PATENT DOCUMENTS 0046859  3/1980  European Pat. Off. .
1180375 10/1963  Fed. Rep. of Germany ...... 564/314
56-22755  3/1981  Japan .......................... 564/314
1241771  8/1971  United Kingdom ............. 564/412

OTHER PUBLICATIONS

Mcomie; "Protective Groups in Organic Chemistry", pp. 75-79 (1973).
Houben-Weyl, "Methoden der Organischen Chemie", vol. 5/3, Halogen Verbindungen Fluoro and Chlor, pp. 873-874 and 884 (1962).

*Primary Examiner*—Richard L. Raymond
*Attorney, Agent, or Firm*—Finnegan, Henderson, Farabow, Garrett, and Dunner

[57] ABSTRACT

A process for producing a chlorohenylhydrazine compound is disclosed, which comprises chlorinating at least one hydrogen atom on the phenyl nucleus in a beta-imidated phenylhydrazine compound and subsequently hydrolyzing the chlorinated compound. Said chlorophenylhydrazine compound is useful as starting material for the production of herbicide, insecticide and photographic coupler is produced in high yield and low cost.

8 Claims, No Drawings

PROCESS FOR PRODUCING CHLOROPHENYLHYDRAZINE COMPOUNDS

BACKGROUND OF THE INVENTION

The present invention relates to a process for producing chlorophenylhydrazine compounds from phenylhydrazine compounds of which the nitrogen atoms on beta-position are protected. More particularly, the present invention relates to a process by which chlorophenylhydrazine compounds which are useful as starting materials for the production of herbicides, insecticides and photographic couplers are produced in high yields from phenylhydrazine compounds of which the nitrogen atoms on beta-position are protected.

Phenylhydrazine compounds having chlorine atoms on the phenyl nucleus (e.g., 2,4,6-trichlorohydrazine) are used as intermediates for the production of such chemicals as herbicides [e.g., propionyl chloride, (2,4,6-trichlorophenyl)hydrazone and isobutyryl(2,4-dichlorophenylhydrazone)] and pyrazolone-type photographic magenta couplers.

The method heretofore used to manufacture chlorophenyl-hydrazine compounds from phenylhydrazine compounds of which the nitrogen atoms on beta-position are protected is described in, for example, J. Humphries, H. Humble, and R. Evans; J. Chem. Soc., 127, 1304–1307 (1925). That is, a particular phenylhydrazine compound is converted to hydrazone by protecting with aldehyde or ketone, then at least one hydrogen atom on the phenyl nucleus is chlorinated and, subsequently, the chlorinated hydrazone is reduced with an appropriate chemical such as zinc. However, zinc which is typically used as a reducing chemical contains cadmium as an impurity, so the post-treatment of the reaction residue is a great concern not only with respect to environmental aspects but also from an economical viewpoint. A further problem is concerned with the aldehyde or ketone which is used as a protective group for the nitrogen atom on beta-position in the phenylhydrazine compound: after reduction such aldehyde or ketone would be eliminated in the form of a compound where the bond to the nitrogen atom on beta-position has been methylated or methylenated. Since the thus eliminated compounds can no longer be reused as a protective group, the cost of the final product will inevitably increase.

SUMMARY OF THE INVENTION

The present invention has been developed under the circumstances described above and the principal object of the invention is to provide a process by which a chlorophenylhydrazine compound can be produced in high yield and at low cost by chlorinating at least one hydrogen atom on the phenyl nucleus in a phenylhydrazine compound having a protected nitrogen atom on beta-position used as a starting material.

Another object of the present invention is to provide a process for producing a chlorophenylhydrazine compound wherein a protective group for the nitrogen atom on beta-position in the phenylhydrazine compound is eliminated under very mild conditions that permit it to be reused efficiently as a protective group.

The aforementioned objects of the present invention can be attained by a process which comprises chlorinating at least one hydrogen atom on the phenyl nucleus in said beta-imidated phenylhydrazine compound, and hydrolyzing the so chlorinated compound.

DETAILED DESCRIPTION OF THE INVENTION

For better understanding of the process of the present invention, a scheme for the production of a typical species of the chlorophenylhydrazine compound is shown below:

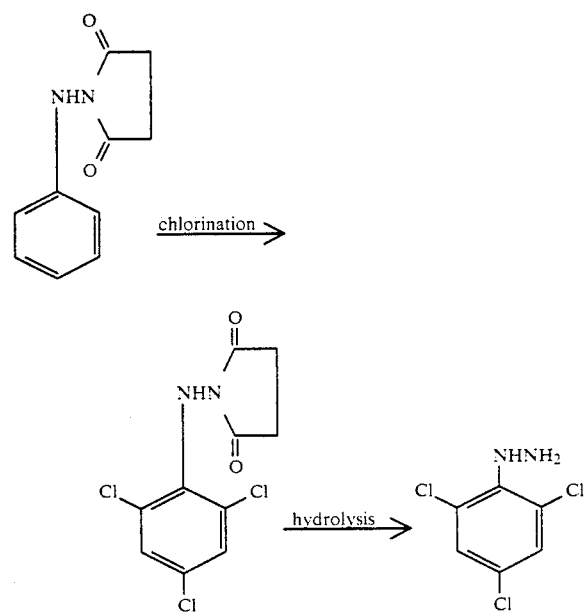

In this scheme, β,β-succinylphenylhydrazine is used as a starting imidated phenylhydrazine compound; however the phenyl nucleus may have a substituent. Succinyl imide moiety is used as an imide moiety. However, a variety of imide moieties such as dicarboxylic acid imide moieties, imide moieties of acids having both a carboxyl radical and.—CSOH radical, imide moieties of acids having two —CSOH radicals, disulfonic acid imide moieties, and imide moieties of acids having both a carboxylic acid and a sulfonic acid can be used as imide moieties.

The chlorophenylhydrazine compound produced by the illustrated scheme is 2,4,6-trichlorophenylhydrazine but it should of course be understood that this compound may be in a mono- or di-chlorinated form. If the chlorophenylhydrazine compound which is the end compound of the process of the present invention is in a trichlorinated form such as 2,4,6-trichlorophenylhydrazine, the phenylhydrazine moiety of the starting β-imidated phenylhydrazine compound may be a chlorophenylhydrazine moiety such as 2-chlorophenylhydrazine moiety, 4-chlorophenylhydrazine moiety or 2,4-dichlorophenylhydrazine moiety. It may also be understood that if the end compound is in a dichlorinated form such as 2,4-dichlorophenylhydrazine, the phenylhydrazine moiety of the starting β-imidated phenylhydrazine compound may be 2-chlorophenylhydrazine moiety, or 4-chlorophenylhydrazine moiety, or an unchlorinated phenylhydrazine moiety. Preferred β-imidated phenylhydrazine compounds are represented by the following general formula:

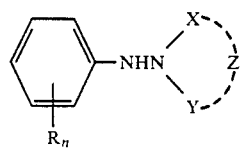

wherein R represents a halogen atom or an organic group such as an alkyl group, an alkoxy group and the like; X and Y each represents a carbonyl, a thiocarbonyl or a sulfonyl group; Z represents an atoms group forming a ring, preferably a 4- to 6-membered ring, and may form a condensed ring, and n is 0 to 4, provided that when n is 2 to 4, each R may be the same or different. R represents preferably a halogen atom or an alkyl group, more preferably a halogen atom, most preferably a chlorine atom.

Specific examples of phenyl nucleus of the β-imidated phenylhydrazine compound which may be used as the starting material in the process of the present invention are listed below:

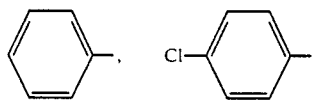

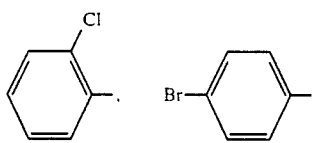

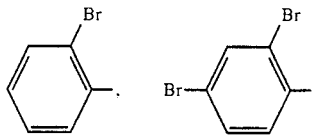

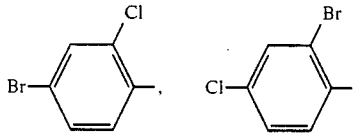

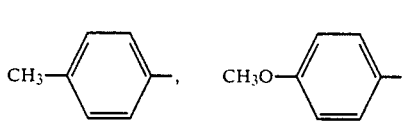

Specific examples of imido moiety of the β-imidated phenylhydrazine compound are listed below:

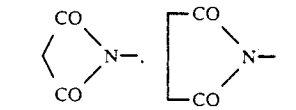

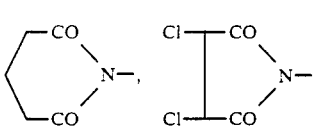

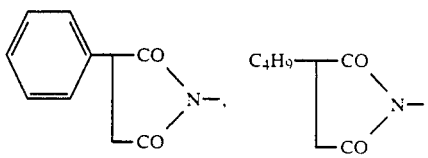

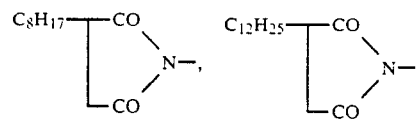

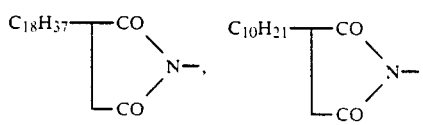

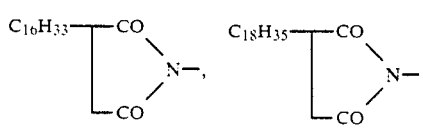

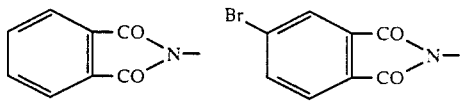

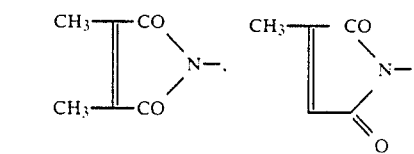

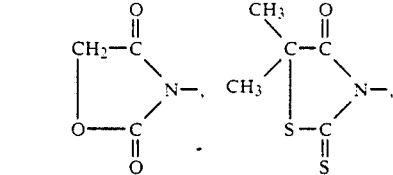

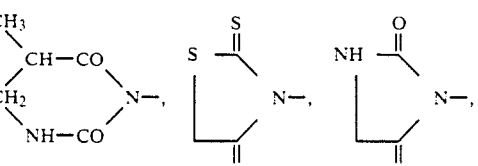

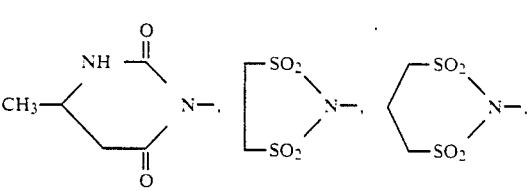

The beta-imidated phenylhydrazine compound may be illustrated, but in no sense limited, by the following examples:

The β-imidated phenylhydrazine compound is preferably subjected to chlorination reaction after it is dissolved or dispersed in a solvent. Typical examples of usable solvents include chloroform, carbon tetrachloride, esters such as ethyl acetate, nitriles such as acetonitrile, aromatic hydrocarbons such as benzene and toluene, sulfuryl chloride, and dimethylformamide.

The beta-imidated phenylhydrazine compound may be chlorinated with any of the chemicals that are commonly employed in chlorination, such as chlorine gas, sulfuryl chloride, hypochlorous acid and salts thereof (e.g., Na and Ca salts). Chloride of lime (a mixture containing calcium hypochlorite) is another example of the chlorinating agent. Sulfuryl chloride may also be used as a solvent.

The amount of the chlorinating agent used varies with the number of chlorine atoms that are to be introduced into the beta-imidated phenylhydrazine compound and, usually, 1-1.1 moles of the chlorinating agent is employed per chlorine atom to be introduced. The number of chlorine atoms introduced into the beta-imidated phenylhydrazine compound means the total number of those chlorine atoms which are introduced into said hydrazine compound at the phenyl nucleus and any other portions (e.g., protective groups), and chlorination of both the phenyl nucleus and other portions of the beta-imidated phenylhydrazine compound is included within the scope of the present invention. However, if sulfuryl chloride is used as a chlorinating agent, it also functions as a solvent and may be used in a large-excess amount, for example, about 6 moles. Even in this case, the number of chlorine atoms introduced may be controlled by adjusting the reaction temperature. For instance, even if 6 moles of sulfuryl chloride is used with a view to allowing it to serve both as a chlorinating agent and as a solvent, a chlorine atom can be introduced into the beta-imidated phenylhydrazine compound on both 2- and 4-positions by performing chlorination at a temperature not higher than about 10° C. If the reaction temperature is selected to be no lower than about 15° C., a chlorine atom may be introduced into the compound on 2-, 4- and 6-positions.

The temperature for chlorinating the beta-imidated phenylhydrazine compound depends on the type of the compound to be chlorinated but is generally in the range of 0°–100° C. The reaction period also depends on the type of the compound to be chlorinated and, in most cases, a period of about 3 hours suffices.

As for the case where the phenyl nucleus in the bata-imidated phenylhydrazine is unsubstituted, a beta-imidated chlorophenylhydrazine compound obtained by the process of the present invention has a chlorine atom introduced as a substituent on the phenyl group on at least one of the 2-, 4- and 6-positions, preferably on both 2- and 4-positions, more preferably on 2-, 4- and 6-positions.

The process of the present invention is particularly effective for introducing a chlorine atom as a substituent at the phenyl nucleus on both 2- and 6-positions.

The beta-imidated chlorophenylhydrazine compound obtained by the process of the present invention is subjected to the next step of hydrolysis either immediately or after being separated from the reaction system.

Water or a water-miscible organic solvent (e.g., methanol or ethanol) may be used as a solvent for hydrolysis. Hydrolytic reaction may be performed in the presence of an acid (e.g., HCl or $H_2SO_4$) or alkali (e.g., NaOH or KOH) reagent. The temperature for hydrolysis is preferably within the range of 50°–120° C., and the period of hydrolysis which depends on the type of the compound to be hydrolyzed and on the reaction temperature is preferably within the range of 3–20 hours. The acid or alkali reagent is preferably used in an amount of at least 1 mole, more preferably at least 2 moles, per mole of the beta-imidated chlorophenylhydrazine compound. Satisfactory results can be obtained by using about 10 moles of the reagent.

Specific examples of the chlorophenylhydrazine compounds obtained according to the process of the present invention are listed below:

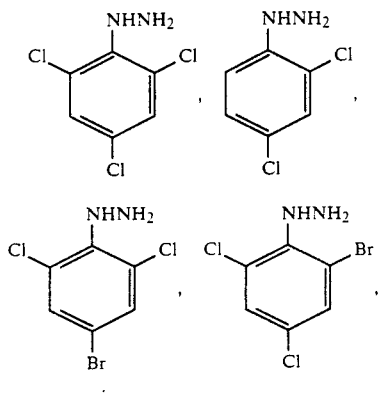

-continued

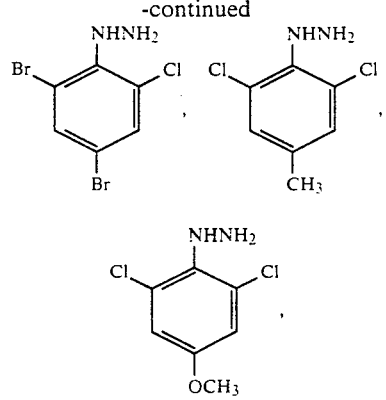

The starting β-imidated phenylhydrazines are readily available as commercial products, or can be prepared by the methods described below.

One method of preparing the β-imidated phenylhydrazine is heating a phenylhydrazine compound which may be a salt such as HCl salts and an acid anhydride in a solvent. This method is described in, for example, Journal of the Chemical Society, 27, 1096.

Specific examples of the phenylhydrazine compounds are listed below:

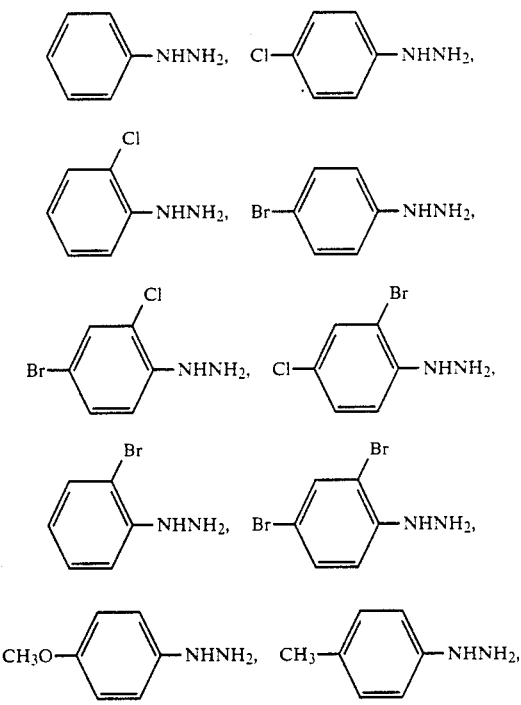

These compounds are readily available as commercial products.

The phenylhydrazine compound is preferably subjected to reaction after it is dissolved or dispersed in a solvent. Typical examples of usable solvents include chloroform, carbon tetrachloride, esters such as ethyl acetate, nitriles such as acetonitrile, aromatic hydrocarbons such as benzene and toluene, and dimethylformamide. Preferable acid anhydrides are cyclic acid anhydrides, with 4- to 6-membered acid anhydrides being particularly preferable. Typical examples of such particularly preferable acid anhydrides are listed below:

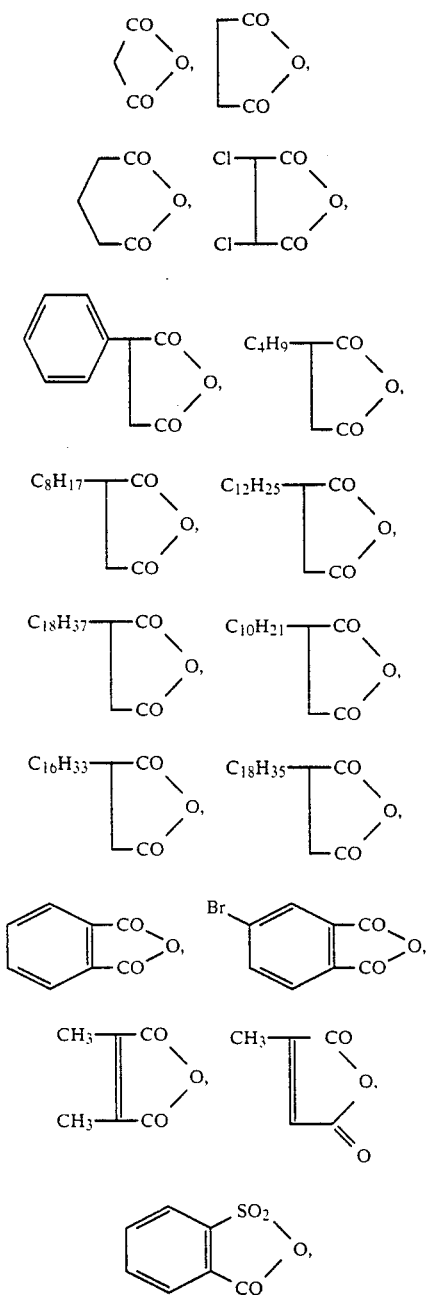

An acid anhydride is preferably added to the reaction solvent either simultaneously or separately from the phenylhydrazine compound. The molar ratio of the phenylhydrazine compound to the acid anhydride preferably ranges from 1:0.8 to 1:1.2.

In order to attain high yields, the phenylhydrazine compound is preferably reacted with the acid anhydride in the presence of an acid. Preferable acids include inorganic acids such as hydrochloric acid, sulfuric acid, phosphoric acid and hydrobromic acid, and organic acids such as organic sulfonic acids (e.g., p-toluenesulfonic acid). One or more of these acids are used in amounts which are preferably at least 0.05 moles, more preferably in the range of 0.05 to 2.0 moles, per mole of the phenylhydrazine compound The acid is introduced into the reaction system preferably no earlier than 5 minutes after initiation of the reaction between the phenylhydrazine compound and the acid anhydride.

The reaction conditions for imidation of the nitrogen atom on beta-position in the phenylhydrazine compound with the acid anhydride are in no way limited but, preferably, the reaction is performed at a temperature between 10° and 180° C. under optional reflux conditions. The reaction temperature after the addition of the acid is preferably of 50°–100° C. The duration of the time during which imidation is completed is preferably from 0.5 to 8 hours, but it is satisfactory for practical purposes to continue the reaction for about 3 hours.

The duration of the reaction which follows the addition of the acid is preferably from 2 to 60 minutes. Another method of preparing β-imidated phenylhydrazine compounds is heating, the monophenylhydrazides of dicarboxylic acids, for example, at a temperature not less than the melting point, or treating the hydrazides with acid.

The hydrazide compounds may be monophenylhydrazides of aliphatic or aromatic dicarboxylic acids.

Preferable compounds are monophenylhydrazide compounds which can be converted to 4- to 6-membered ring imide compounds.

Specific examples of the monohydrazide of the dicarboxylic acid are listed below:

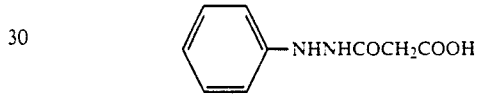

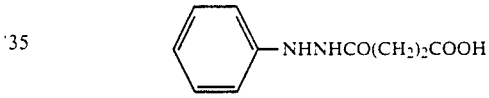

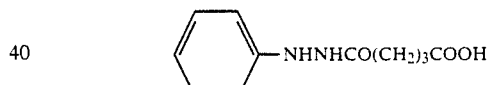

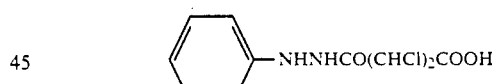

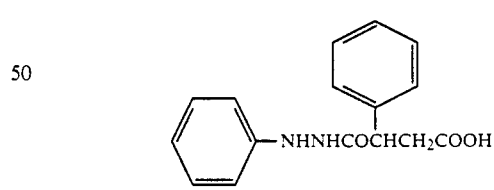

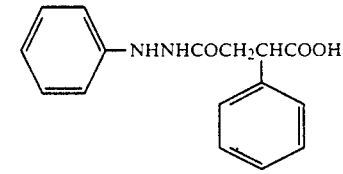

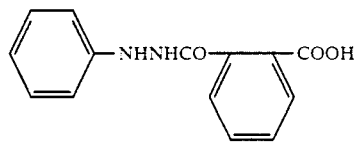

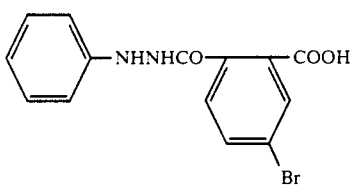
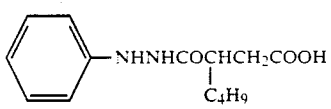
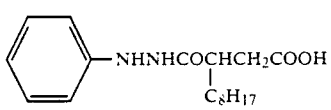
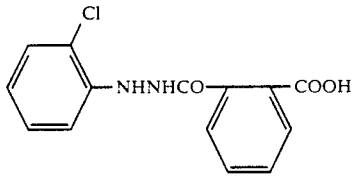
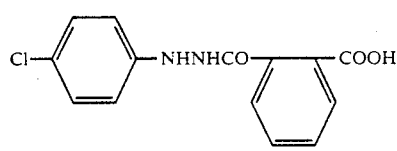
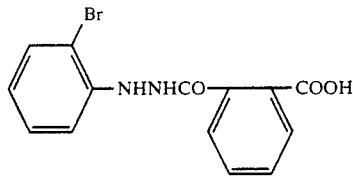
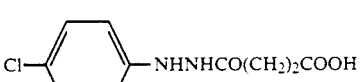
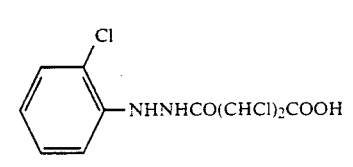
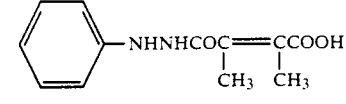

In treating the hydrazide compound with acid, the hydrazide compound is preferably subjected to reaction after it is dissolved or dispersed in a solvent.

Typical examples of the usable solvent include chloroform, carbon tetrachloride, esters such as ethyl acetate, nitriles such as acetonitrile, aromatic hydrocarbons such as benzene and toluene, and dimethylformamide.

Any acid may be employed but preferable examples include inorganic acids such as hydrochloric acid, sulfuric acid, phosphoric acid and hydrobromic acid, and organic acids such as organic sulfonic acids (e.g., p-toluenesulfonic acid). One or more of these acids are used in amounts which are preferably at least 0.05 moles, more preferably in the range of 0.05 to 2.0 moles, per mole of the hydrazide.

The reaction conditions are in no way limited but, preferably, the reaction is performed at a temperature between 20° and 180° C. under optional reflux conditions, more preferably in the range of 50°–100° C.

The duration of the reaction is preferably from 2 to 60 minutes.

Another method of preparing β-imidated phenylhydrazine compounds is treating the phenylhydrazine compounds with dicarboxylic acid halogenides.

Specific examples of the dicarboxylic acid halogenide are listed below:

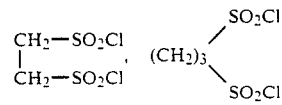

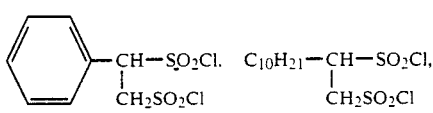

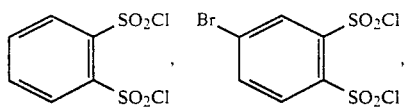

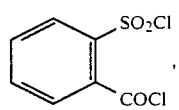

Preferably a phenylhydrazine compound and an acid halogenide each are dissolved or dispersed in solvents.

In general, an acid halogenide solution is poured into a phenylhydrazine compound solution little by little. However, according to circumstances, an acid halogenide solution may be poured all at one time. It is preferable that the reaction is performed in the presence of a base as an acid scavenger, for example, an organic base such as pyridine and triethylamine, or an inorganic base such as sodium carbonate and potassium carbonate. The base is preferably used in an amount 1.1 or more times that of acid to be produced on the reaction.

The molar ratio of the phenylhydrazine compound to the acid halogenide preferably ranges from 1:0.8 to 1:1.2.

The reaction temperature is in no way limited, but is preferably between −15° and 120° C. under optional reflux conditions. An acid halogenide solution is preferably poured at a low temperature.

The reaction period depends on the type of the compound used and the reaction temperature but is, in most cases, 30 minutes to 15 hours.

ADVANTAGES OF THE INVENTION

According to the process of the present invention, at least one hydrogen atom on the phenyl nucleus of a beta-imidated phenylhydrazine compound is chlorinated, and the so chlorinated compound is subsequently hydrolyzed.

By these procedures, a chlorophenylhydrazine compound which is useful as an intermediate for the production of herbicides or photographic couplers can be obtained at low cost and in high yield. During hydrolysis, the protective groups are eliminated in the form of a dibasic acid which may be repeatedly used readily or after being converted to an acid halogenide or an acid anhydride by an appropriate means (e.g., halogenation by thionyl chloride, dehydration by heating) as an imidating agent to obtain a β-imidated phenylhydrazine compound. Another advantage of the process of the present invention is that a chlorophenylhydrazine compound having a chlorine atom on both 2- and 6-positions of the phenyl nucleus (e.g., 2,4,6-trichlorophenylhydrazine) can also be produced in high yield and at low cost and the chlorophenylhydrazine compound obtained is very pure.

EXAMPLE 1: Preparation of trichlorophenylhydrazine

Succinic anhydride (100 g) was added to ethyl acetate (2,000 ml) solution of phenylhydrazine (108 g) at room temperature under agitation. A white crystal has precipitated The mixture was stirred for 3 hours and heated under reflux for 3 hours. Subsequently, concentrated sulfuric acid (45 g) was poured into the reaction mixture. Five minutes later, the mixture was cooled down to room temperature with water.

The cooled reaction mixture was washed successively with water, an aqueous alkali solution (16 g of sodium carbonate in 160 ml of water) and an aqueous sodium chloride solution. Then, the washed mixture was evaporated to dryness under vacuum and the solid residue was suspended in heated ethanol (250 ml). The suspension was cooled and passed through a filter to obtain 152 g of β,β-succinylphenylhydrazine (m.p. 155° C.). Yield: 80%.

The so obtained β,β-succinylphenylhydrazine (190 g) was gradually added to 810 g of sulfuryl chloride under cooling with water. Vigorous reaction occurred and the hydrazine dissolved with evolution of HCl and SO₂ gases. Thereafter, the mixture was stirred at room temperature (25°±5° C.) for one hour, thereby completing the chlorination of the hydrazine. The residual excess sulfuryl chloride was recovered by atmospheric distillation. Further distillation under vacuum produced a brown syrupy residue in an amount of 288 g (yield, 98%).

To the syrup, 1,000 ml of methanol and 330 ml of conc. HCl were added and the mixture was refluxed under agitation for 5 hours so as to complete hydrolysis. Methanol was recovered by atmospheric distillation. Further distillation under vacuum produced a brown residual powder. An aqueous alkali solution (215 g of NaOH in 600 ml of water) was immediately added to the residue and the mixture was vigorously agitated for 20 minutes at 60°±10° C. After cooling with water, the crystal of the end compound was recovered by filtration, washed with water and dried to obtain 185 g of 2,4,6-trichlorophenylhydrazine as a pale brownish white powder (m.p. 140°–141° C.). Yield: 89%.

The β,β-succinylphenylhydrazine obtained by the way described below was used in place of that obtained above. The result was similarly good.

The mixture of succinic acid monophenylhydrazide (208 g), ethyl acetate (2,000 ml) and concentrated sulfuric acid (45 g) was heated under reflux for 5 minutes. After the reaction mixture was cooled down to room temperature with water, the cooled mixture was washed successively with water, an aqueous alkali solution (16 g of sodium carbonate in 160 ml of water) and an aqueous sodium chloride solution Then, the washed mixture was evaporated to dryness under vacuum and the solid residue was suspended in heated ethanol (250 ml). The suspension was cooled and passed through a filter to obtain 160 g of β,β-succinylphenylhydrazine (m.p. 155° C.). Yield: 84%.

EXAMPLE 2: Synthesis of 2,4,6-trichlorophenylhydrazine

Phthalic anhydride (148 g) was added to a mixture of phenylhydrazine (108 g) and acetonitrile (1,000 ml) and the resulting mixture was agitated for 2 hours at room temperature. After refluxing for 1 hour, 20 g of conc sulfuric acid was added and the mixture was refluxed for 20 minutes.

Subsequently, the solvent was recovered by atmospheric distillation. After further distillation under vacuum, ethyl acetate (2,000 ml) was added to the residue. The mixture was worked up as in Example 1 to obtain 190 g of N-phthaliminoaniline (m.p. 178°–180° C.) in a yield of 82.6%.

Sulfuryl chloride (800·g) was added to a mixture of the N-phthaliminoaniline (238 g) and carbon tetrachloride (1,000 ml). After reaction was caused to occur by gradual heating, the mixture was refluxed for 2 hours and the solvent was recovered by atmospheric distillation and vacuum distillation. To 333 g of the resulting residue (yield, 98%), 1,300 ml of ethyl alcohol and 330 ml of conc. hydrochloric acid were added and the mixture was refluxed for 5 hours. The solvent was subsequently recovered by distillation, first at atmospheric pressure, then under vacuum. The resulting residue which still contained a small amount of water was rendered alkaline by addition of 1,300 ml of an aqueous alkali solution (240 g of NaOH in 600 ml of water) and stirred to produce a pale brown precipitate. After cooling with water, the pale brown precipitate was recovered by filtration, washed with water 20 and dried to obtain 185 g of the end compound, 2,4,6-trichlorophenylhydrazine as a pale brown powder (m.p. 139°–141° C.) in a yield of 93%.

The N-phthaliminoaniline obtained by the way described below was used in place of that obtained above. The result was similarly good.

The mixture of phthalic acid monophenylhydrazide (256 g), acetonitrile (1,000 ml) and concentrated sulfuric acid was heated under reflux for 20 minutes. The solvent was recovered by atmospheric distillation and vacuum distillation.

After ethyl acetate (2,000 ml) was added to the residue, the mixture was washed successively with water, an aqueous alkali solution (16 g of sodium carbonate in 160 ml of water) and an aqueous sodium chloride solution. Then the washed mixture was evaporated to dryness under vacuum and solid residue was suspended in heated ethanol (250 ml). The suspension was cooled and passed through a filter to obtain 195 g of phthaliminoaniline (m.p. 178°-280° C.). Yield: 82%.

EXAMPLE 3: Synthesis of 2,4,6-trichlorophenylhydrazine

The procedures of Example 1 were repeated except using an α-octyl succinicanhydride in place of the succinicanhydride. The result was similarly good.

EXAMPLE 4: Synthesis of 2,4,6-trichlorophenylhydrazine

Two hundred and ten grams of N-(α,α'-dichlorosuccinylimino)aniline (yield, 81%) was obtained as in Example 1 except that the succinicanhydride was replaced by 169 g of α,α'-dichlorosuccinic anhydride. Chlorine gas was passed through 259 g of the N-(α,α'-dichlorosuccinylimino)aniline in 3,000 ml of carbon tetrachloride. Thereafter, the solvent was recovered by distillation, first at atmospheric pressure, then under vacuum. The reaction product was obtained in an amount of 355 g (yield, 98%). After addition of methanol ($1.2 \times 10^3$ ml) and 30% aqueous $H_2SO_4$ (660 ml), the reaction product was refluxed for 8 hours. The mixture was subsequently worked up as in Example 1 to obtain 180 g of the end compound, 2,4,6-trichlorophenylhydrazine, as a pale brown powder (m.p. 139°-141° C.) in a yield of 87%.

215 g of N-(α,α'-dichlorosuccinylimino)aniline, which was obtained by using an α,α'-dichlorosuccinic acid monophenylhydrazide (277 g) in place of the succinic acid monophenylhydrazide in Example 1, was used in place of that obtained above. The result was similarly good.

EXAMPLE 5: Synthesis of 2,4-dichlorophenylhydrazine

The procedures of Example 1 were repeated except that the amount of sulfuryl chloride was changed to 2 moles per mole of β,β-succinylphenylhydrazine. The end compound (m.p. 90°-92° C.) was obtained in an amount of 130 g (yield, 73%).

When the procedures of Example 1 were repeated with the reaction temperature being held at between 0° and 5° C. after the addition of sulfuryl chloride, the end compound (m.p. 90°-91° C.) was obtained in an amount of 133 g.

EXAMPLE 6: Preparation of trichlorophenylhydrazine 19.2 g of 3-anilinorhodanine represented by the formula below, which was prepared by the way described in (F. C. Brown) J.O.C. 24 1060 (1959), was gradually added to 81 g of sulfuryl chloride under agitation and under cooling with water.

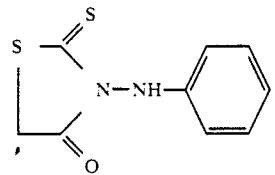

Vigorous reaction occurred and the 3-anilinorhodanine dissolved with evolution of HCl and $SO_2$ gases.

Thereafter, the mixture was stirred at room temperature (25°±5° C.) for one hour, thereby completing the chlorination. The residual excess sulfuryl chloride was recovered by atmospheric distillation. Further distillation under vacuum produced a brown syrupy residue. To the syrup, sodium hydrooxide solution (10 g of NaOH in 200 ml of ethanol) was added for hydrolysis and the mixture was refluxed under agitation for 5 hours.

After adding 17 ml of conc. hydrochloric acid to neutralize, ethanol was recovered under vacuum distillation. The residual brown powder was suspended in water and the suspension was passed through a filter to obtain the powder. After drying, the powder was recrystalized from ethanol. 19 g of 2,4,6-trichlorophenylhydrazine was obtained as white powder (m.p. 140°-141° C.).

EXAMPLE 7: Synthesis of 2,4,6-trichlorophenylhydrazine

The chlorination procedures of Example 6 were repeated, except using 19.1 g of 3-anilinohydantoin prepared by the way described in (H. Bavard Milne, Duane W. Fish) J.O.C., 27 3177-3182 (1962) in place of 19.2 g of 3-anilinorhodanine.

After alkali hydrolysis, the reaction mixture was added with hydrochloric acid to acidify. After filtration, the residue was washed with water and was refluxed in 200 ml of ethanol and 15 ml of conc. hydrochloric acid for 4 hours.

After neutralization with alkali, the ethanol was recovered under vacuum distillation. After the residue was washed with water and dried, the residue was recrystallized in ethanol to obtain 15 g of 2,4,6-trichlorophenylhydrazine.

EXAMPLE 8: Synthesis of 2,4,6-trichlorophenylhydrazine

The chlorination and hydrolysis procedures of Example 7 were repeated except using 21.9 g of 3-anilino-6-methyldihydropyrimidine-2, 4-dion prepared by the way described in (K. Schloegl) Monatsh, 89 61-73 (1958) in place of 19.1 g of 3-anilinohydantoin. 17 g of 2,4,6-trichlorophenylhydrazine was obtained by recrystallization with ethanol.

EXAMPLE 9: Synthesis of 2,4,6-trichlorophenylhydrazine 24 g of o-chlorocarbonylbenzenesulfonylchloride dissolved in 70 ml acetonitrile was gradually added to a mixture of 10.8 g of phenylhydrazine, 100 ml of acetonitrile and 20 g of pyridine.

After the reaction was performed, the solvent was distilled for 6 hours at room temperature. To the residue, 300 ml of ethylacetate was added and the mixture was washed with water. Ethylacetate was distilled and the residue was recrystallized with ethanol to obtain 18 g of 2-anilinosaccharine (d.p. 195°–200° C.).

This product was added into 90 g of sulfuryl chloride and the reaction was performed for 2 hours at room temperature. The sulfuryl chloride in excess was recovered by atmospheric distillation and vacuum distillation to obtain crude 2-(2,4,6-trichloroanilino)-saccharine.

This product was mixed with 120 ml of ethanol and 30 ml of conc. hydrochloric acid and the mixture was refluxed for 6 hours for hydrolysis. After the solvent was distilled, 90 ml of water and 15 g of NaOH were added to the residue. The precipitate was filtered, washed with water and dried
to obtain 11 g of 2,4,6-trichlorophenylhydrazine (m.p. 140°–142° C.) as pale brown powder.

EXAMPLE 10: Synthesis of 2,4,6-trichlorophenylhydrazine

The procedures of Example 9 were repeated except using 28 g of o-chlorosulfonylbenzenesulfonylchloride in place of the o-chlorocarbonyl benzenesulfonyl-chloride and chlorine gas in chloroform in place of the sulfuryl chloride, to obtain 12 g of 2,4,6-trichlorophenylhydrazine.

What is claimed is:

1. A process for producing a chlorophenylhydrazine compound which comprises chlorinating at least one hydrogen atom on the phenyl nucleus in a beta-imidated phenylhydrazine compound and subsequently hydrolyzing the chlorinated compound.

2. A process according to claim 1, wherein the chlorination is performed with a sulfuryl chloride.

3. A process according to claim 1, wherein the beta-imidated phenylhydrazine compound is a $\beta,\beta$-succinylphenylhydrazine.

4. A process according to claim 1, wherein the beta-imidated phenylhydrazine compound is a $\beta,\beta$-octylsuccinylphenylhydrazine.

5. A process according to claim 1, wherein the beta-imidated phenylhydrazine compound is obtained by imidating a phenylhydrazine compound with a dicarboxylic acid anhydride.

6. A process according to claim 5, wherein the dicarboxylic acid anhydride is a succinic acid anhydride.

7. A process according to claim 5, wherein the dicarboxylic acid anhydride is an $\alpha$-octyl succinic anhydride.

8. A process according to claim 5, wherein the imidating process is performed in the presence of an inorganic acid.

* * * * *

UNITED STATES PATENT AND TRADEMARK OFFICE
CERTIFICATE OF CORRECTION

PATENT NO. : 5,041,667
DATED : August 20, 1991
INVENTOR(S) : Mitsuto Fujiwhara et al.

It is certified that error appears in the above-identified patent and that said Letters Patent is hereby corrected as shown below:

Abstract, line 1, change "chlorohenylhydrazine" to --chlorophenylhydrazine--.

"Claim 4, column 20, lines 12 and 13, change "$\beta,\beta$-octylsuccinylphenylhydrazine" to --$\beta,\beta$-$\alpha$-octylsuccinylphenylhydrazine--.".

Signed and Sealed this

Eighth Day of June, 1993

Attest:

MICHAEL K. KIRK

Attesting Officer

Acting Commissioner of Patents and Trademarks